(12) United States Patent
Collins et al.

(10) Patent No.: US 10,835,255 B2
(45) Date of Patent: Nov. 17, 2020

(54) ADAPTER ASSEMBLIES FOR INTERCONNECTING ELECTROMECHANICAL HANDLE ASSEMBLIES AND SURGICAL LOADING UNITS

(71) Applicant: Covidien LP, Mansfield, MA (US)

(72) Inventors: Ethan Collins, Naugatuck, CT (US); Paul Richard, Shelton, CT (US); Anthony Calderoni, Bristol, CT (US); John Hryb, Southington, CT (US)

(73) Assignee: Covidien LP, Mansfield, MA (US)

( * ) Notice: Subject to any disclaimer, the term of this patent is extended or adjusted under 35 U.S.C. 154(b) by 438 days.

(21) Appl. No.: 15/421,798

(22) Filed: Feb. 1, 2017

(65) Prior Publication Data
US 2017/0224347 A1    Aug. 10, 2017

Related U.S. Application Data

(60) Provisional application No. 62/293,500, filed on Feb. 10, 2016.

(51) Int. Cl.
*A61B 17/115*    (2006.01)
*A61B 90/90*    (2016.01)
(Continued)

(52) U.S. Cl.
CPC .... *A61B 17/1155* (2013.01); *A61B 17/00234* (2013.01); *A61B 17/068* (2013.01);
(Continued)

(58) Field of Classification Search
CPC .......... A61B 17/1155; A61B 17/00234; A61B 17/068; A61B 17/11; A61B 17/115;
(Continued)

(56) References Cited

U.S. PATENT DOCUMENTS 5,947,764 A * 9/1999 Pan ........................ H01R 12/57
439/492
8,734,476 B2   5/2014 Rhee et al.
(Continued)

FOREIGN PATENT DOCUMENTS

CN    101902972 A    12/2010
CN    105078531 A    11/2015
(Continued)

OTHER PUBLICATIONS

European Search Report, dated Jun. 28, 2017, corresponding to European Application No. 17155483.5; 8 pages.
(Continued)

*Primary Examiner* — Chelsea E Stinson
*Assistant Examiner* — Mary C Hibbert-Copeland
(74) *Attorney, Agent, or Firm* — Carter, DeLuca & Farrell LLP

(57) ABSTRACT

A surgical instrument includes a handle assembly and an adapter assembly. The handle assembly includes a handle housing and a processor disposed within the handle housing. The adapter assembly includes a knob housing, an elongate body, a plurality of electrical components, and a flex circuit. The knob housing is configured to be connected to the handle housing. The elongate body extends distally from the knob housing and has a distal end configured to be coupled to an end effector. The electrical components are disposed within the elongate body. The flex circuit has a proximal end configured to be electrically connected to the processor, and a distal end configured to be electrically connected to the electrical components.

20 Claims, 6 Drawing Sheets

(51) Int. Cl.
  *A61B 17/00* (2006.01)
  *A61B 17/068* (2006.01)
  *A61B 17/11* (2006.01)
  *A61B 90/00* (2016.01)

(52) U.S. Cl.
  CPC ............ *A61B 17/11* (2013.01); *A61B 17/115* (2013.01); *A61B 90/90* (2016.02); *A61B 2017/00017* (2013.01); *A61B 2017/00398* (2013.01); *A61B 2017/00464* (2013.01); *A61B 2017/00482* (2013.01); *A61B 2017/00734* (2013.01); *A61B 2017/1132* (2013.01); *A61B 2090/0808* (2016.02); *A61B 2562/0247* (2013.01); *A61B 2562/0261* (2013.01)

(58) Field of Classification Search
  CPC ........... A61B 2017/00017; A61B 2017/00398; A61B 2017/00464; A61B 2017/00482; A61B 2017/00734; A61B 2017/1132
  USPC ............................................ 227/176.1–180.1
  See application file for complete search history.

(56) References Cited

U.S. PATENT DOCUMENTS

| | | |
|---|---|---|
| 9,023,014 B2 | 5/2015 | Chowaniec et al. |
| 2006/0079879 A1 | 4/2006 | Faller et al. |
| 2009/0030312 A1 | 1/2009 | Hadjicostis |
| 2009/0090763 A1* | 4/2009 | Zemlok ............ A61B 17/07207 227/175.2 |
| 2011/0022032 A1 | 1/2011 | Zemlok et al. |
| 2011/0121049 A1 | 5/2011 | Malinouskas et al. |
| 2011/0218484 A1 | 9/2011 | Zemlok et al. |
| 2012/0078278 A1 | 3/2012 | Bales, Jr. et al. |
| 2013/0137954 A1 | 5/2013 | Jacobsen et al. |
| 2013/0289592 A1* | 10/2013 | Stulen ............ A61B 17/320092 606/169 |
| 2013/0324978 A1 | 12/2013 | Nicholas et al. |
| 2013/0343011 A1 | 12/2013 | Heinrich et al. |
| 2014/0207124 A1 | 7/2014 | Aldridge et al. |
| 2015/0366560 A1* | 12/2015 | Chen ...................... A61B 17/00 227/176.1 |
| 2016/0274962 A1 | 9/2016 | Fortune et al. |

FOREIGN PATENT DOCUMENTS

| | | |
|---|---|---|
| CN | 105212979 A | 1/2016 |
| EP | 2301468 A1 | 3/2011 |
| EP | 2932910 A2 | 10/2015 |
| WO | 2009/039506 A1 | 3/2009 |
| WO | 2014/116961 A1 | 7/2014 |

OTHER PUBLICATIONS

Chinese Office Action (with English Summary) dated Jul. 3, 2020, corresponding to counterpart Chinese Application No. 201710071492.7; 28 total pages.

* cited by examiner

ADAPTER ASSEMBLIES FOR INTERCONNECTING ELECTROMECHANICAL HANDLE ASSEMBLIES AND SURGICAL LOADING UNITS

CROSS-REFERENCE TO RELATED APPLICATIONS

This application claims the benefit of and priority to U.S. Provisional Patent Application No. 62/293,500 filed Feb. 10, 2016, the entire disclosure of which is incorporated by reference herein.

BACKGROUND

1. Technical Field

The present disclosure relates to adapter assemblies to electrically and mechanically interconnect electromechanical handle assemblies and surgical loading units. More specifically, the present disclosure relates to flex circuits of adapter assemblies for electrically interconnecting handle assemblies, adapter assemblies, and/or surgical loading units.

2. Background of Related Art

A number of surgical device manufacturers have developed product lines with proprietary drive systems for operating and/or manipulating electromechanical surgical devices. In many instances, the electromechanical surgical devices included a handle assembly, which was reusable, and disposable loading units and/or single use loading units or the like. The loading units included an end effector disposed at an end thereof that were selectively connected to the handle assembly prior to use and then disconnected from the handle assembly following use in order to be disposed of or in some instances sterilized for re-use.

In certain instances, an adapter assembly was used to interconnect an electromechanical surgical device with any one of a number of surgical attachments, such as, for example, surgical loading units or end effectors, to establish a mechanical and/or electrical connection therebetween. To form an electrical connection between the handle assembly, adapter assembly, and surgical loading unit, a plurality of discreet wires were used.

A need exists for an improved way to electrically interconnect components of a surgical instrument.

SUMMARY

The present disclosure relates the flex circuits that are incorporated into adapter assemblies of electromechanical surgical systems. The flex circuits are configured for electrically interconnecting handle assemblies and surgical loading units.

According to an aspect of the present disclosure, a surgical instrument is provided that includes a handle assembly and an adapter assembly. The handle assembly includes a handle housing and a processor disposed within the handle housing. The adapter assembly includes a knob housing, an elongate body, a plurality of electrical components, and a flex circuit. The knob housing is configured to be connected to the handle housing. The elongate body extends distally from the knob housing and has a distal end configured to be coupled to an end effector. The electrical components are disposed within the elongate body. The flex circuit has a proximal end configured to be electrically connected to the processor, and a distal end configured to be electrically connected to the electrical components.

In some embodiments, the flex circuit may have a first surface layer and a second surface layer stacked upon one another. The first surface layer may be configured to electrically couple the processor to two of the plurality of electrical components. The second surface layer may be configured to electrically couple the processor to another of the plurality of electrical components.

It is contemplated that the distal end of the flex circuit may have a switch configured to be activated by one type of end effector upon connection of the end effector to the distal end of the elongate body.

It is envisioned that one of the electrical components may be a linear position sensor assembly that is disposed in the distal end of the elongate body. The distal end of the flex circuit may be electrically connected to the linear position sensor assembly. The linear position sensor assembly may include a plurality of sensors axially aligned with one another along a longitudinal axis of the linear position sensor assembly. The linear position sensor assembly may have five contacts electrically connected to the distal end of the flex circuit.

In some aspects of the present disclosure, one of the electrical components may be a pressure sensor. The distal end of the flex circuit may be bifurcated, forming a first distal end electrically connected to the linear position sensor assembly and a memory, and a second distal end electrically connected to the pressure sensor. The pressure sensor may be a strain gauge. The pressure sensor may have five contacts electrically connected to the second distal end of the flex circuit.

In some embodiments, one of the electrical components may be a memory having stored therein an operating parameter of the surgical instrument. The distal end of the flex circuit may be electrically connected to the memory. The operating parameter may be selected from the group consisting of a speed of operation of a motor of the handle assembly, an amount of power to be delivered by the motor of the handle assembly during operation thereof, a selection of motors of the handle assembly to be actuated, and a type of function of an end effector to be performed by the handle assembly. The memory may have an identification code stored therein corresponding to one type of end effector. The memory may be a 1-wire eeprom. The 1-wire eeprom may have two contacts electrically connected to the distal end of the flex circuit.

In another aspect of the present disclosure, a surgical instrument is provided that includes a handle assembly, an adapter assembly, and a surgical loading unit. The handle assembly includes a handle housing. A motor and a processor are each disposed within the handle housing. The adapter assembly includes a knob housing configured to be connected to the handle housing, an elongate body extending distally from the knob housing, a plurality of electrical components disposed within the elongate body, and a flex circuit. The flex circuit has a proximal end and a distal end. The proximal end of the flex circuit is configured to be electrically connected to the processor. The distal end is configured to be electrically connected to the electrical components. The surgical loading unit has a proximal end and a distal end. The proximal end of the surgical loading unit is configured to be operably coupled to a distal end of the elongate body of the adapter assembly. The distal end of the surgical loading unit has an end effector.

In some embodiments, the distal end of the flex circuit may have a switch configured to be activated by the surgical loading unit upon connection of the surgical loading unit to the adapter assembly such that upon connecting the surgical loading unit with the adapter assembly, the memory automatically transmits at least one operating parameter to the processor via the flex cable.

BRIEF DESCRIPTION OF THE DRAWINGS

Embodiments of the present disclosure are described herein with reference to the accompanying drawings, wherein.

DETAILED DESCRIPTION

Figure 1:
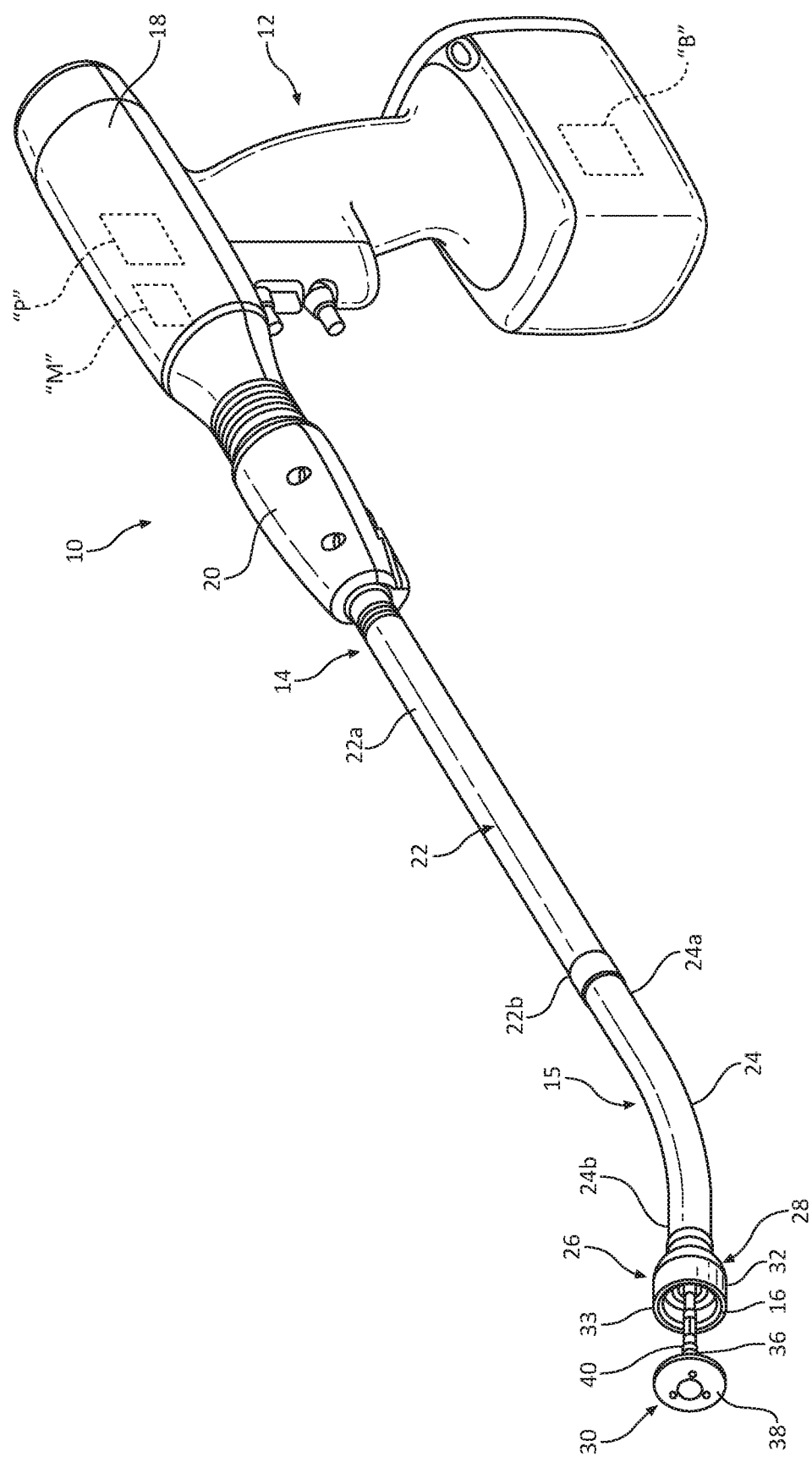
FIG. 1 is a perspective view of a hand-held, electromechanical surgical instrument, in accordance with an embodiment of the present disclosure.

Embodiments of the presently disclosed electromechanical surgical instruments including handle assemblies, adapter assemblies, and surgical loading units including end effectors are described in detail with reference to the drawings, in which like reference numerals designate identical or corresponding elements in each of the several views. As used herein the term "distal" refers to that portion of the handle assembly, adapter assembly, surgical loading unit or components thereof, farther from the user, while the term "proximal" refers to that portion of the handle assembly, adapter assembly, surgical loading unit or components thereof, closer to the user.

Figure 2:
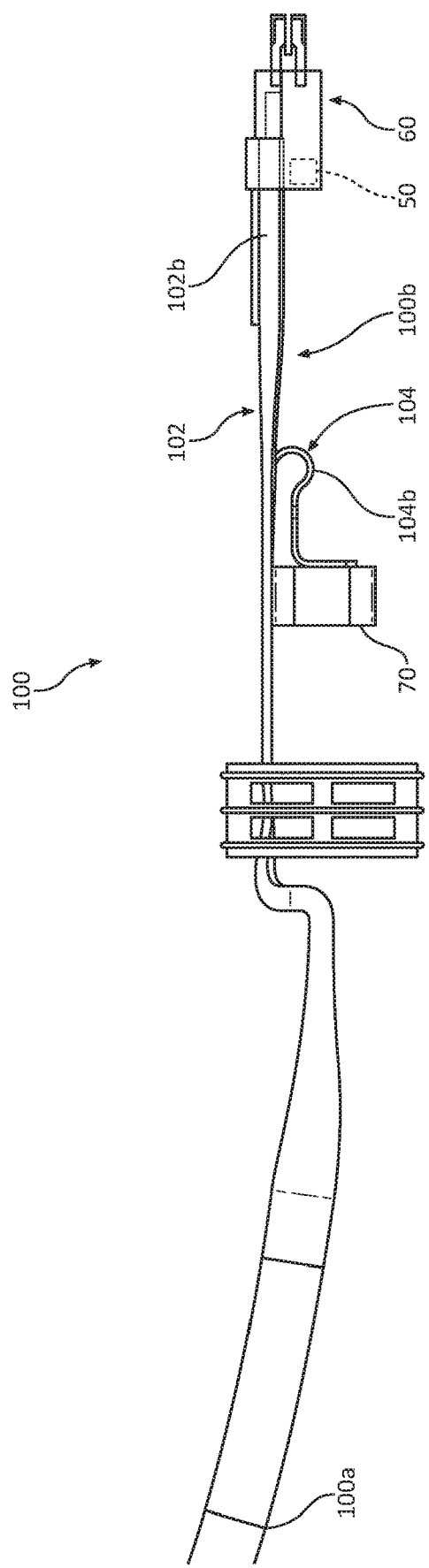
FIG. 2 is a side view of a flex circuit for electrically interconnecting a handle assembly of the surgical instrument of FIG. 1 and an adapter assembly of the surgical instrument of FIG. 1.
Figure 3A:
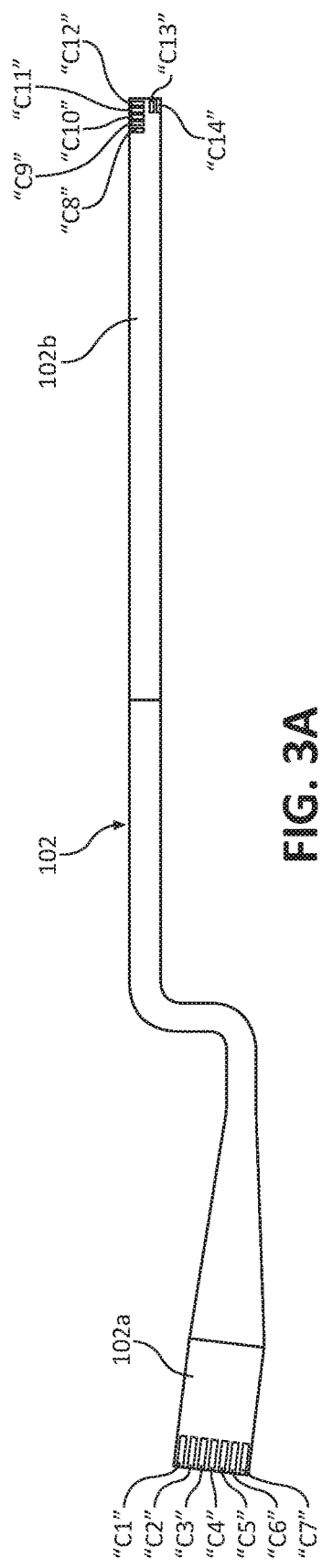
FIG. 3A is a side view of a first surface layer of the flex circuit of FIG. 2, with parts removed.
Figure 3B:
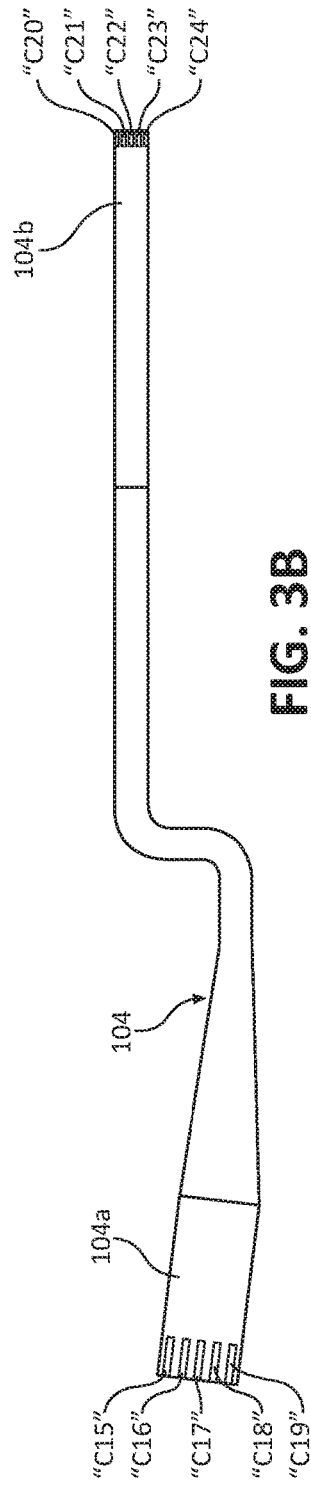
FIG. 3B is a side view of a second surface layer of the flex circuit of FIG. 2, with parts removed.
Figure 3C:
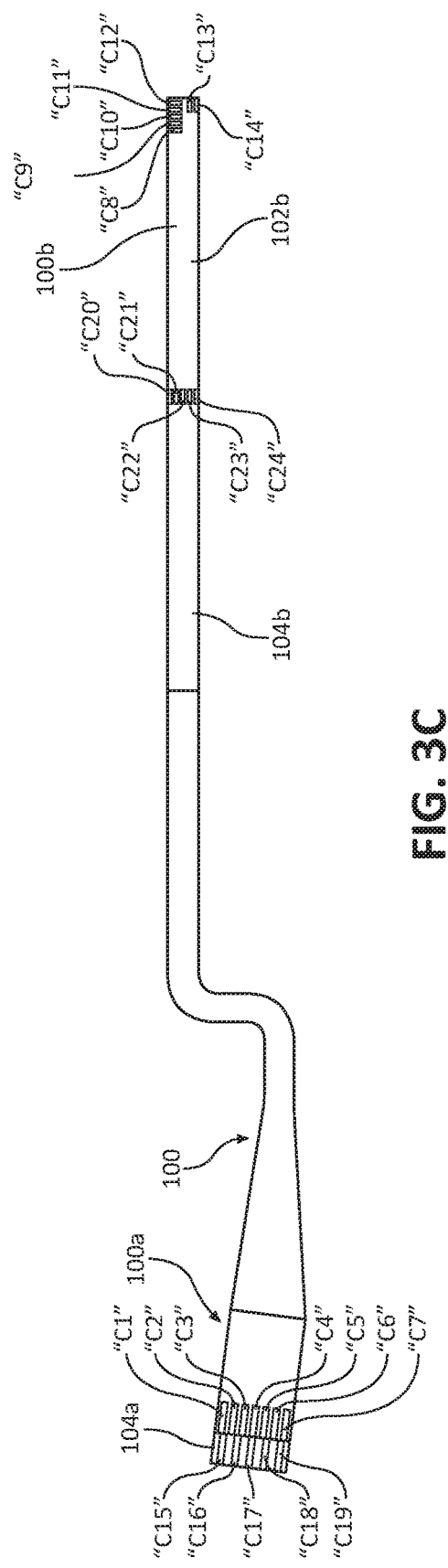
FIG. 3C is a side view of the first and second surface layers of flex circuit of FIGS. 3A and 3B, respectively, attached to one another.

With brief reference to FIG. 2, a flexible circuit or flex circuit 100 is provided and is configured for receipt in an adapter assembly 14 (FIG. 1). Flex circuit 100 electrically interconnects a processor "P" (FIG. 1) of a handle assembly 12 (FIG. 1) and a plurality of electrical components of adapter assembly 14 (FIG. 1). The electrical components include, but are not limited to, a memory, a linear position sensor assembly, and/or a pressure sensor, as will be described in detail herein. The flex circuit 100 is easy to assemble within adapter assembly 14, eliminates the need for discreet, separate wires, and ultimately enhances patient safety and reduces manufacturing costs.

With reference to FIG. 1, a surgical instrument is provided, such as, for example, an electromechanical surgical instrument designated generally using reference character 10. Surgical instrument 10 generally includes a handle assembly 12, an adapter assembly 14, and a surgical loading unit 15 having an end effector 26. Handle assembly 12 is configured for selective attachment to any one of a number of adapter assemblies, for example, the illustrated circular end-to-end anastomosis adapter assembly 14 or an endo-gastrointestinal anastomosis adapter assembly (not shown), and, in turn, each adapter assembly is configured for selective connection with any number of surgical loading units, such as, for example, the illustrated circular end-to-end anastomosis surgical loading unit 15 or an endo-gastrointestinal anastomosis surgical loading unit (not shown). Surgical loading unit 15 and adapter assembly 14 are configured for actuation and manipulation by handle assembly 12. Upon connecting adapter assembly 14 to handle assembly 12 and one type of surgical loading unit 15 to adapter assembly 14, powered, hand-held, electromechanical surgical instrument 10 is formed.

For a detailed description of the construction and operation of an exemplary electromechanical, hand-held, powered surgical instrument, reference may be made to International Publication No. WO 2009/039506, filed on Sep. 22, 2008, and U.S. Patent Application Publication No. 2011/0121049, filed on Nov. 20, 2009, the entire contents of each of which are incorporated herein by reference.

With continued reference to FIG. 1, handle assembly 12 includes an inner core handle assembly (not explicitly shown) and a handle housing or shell 18 configured to selectively receive and encase the inner core handle assembly. It is contemplated that handle housing 16 may be disposable or sterilizable for re-use. The inner core handle assembly includes one or more motors "M" operable and configured to drive an operation of end effector 26 of surgical loading unit 15. The inner core handle assembly has a plurality of sets of operating parameters (e.g., speed of operation of motors "M" of handle assembly 12, an amount of power to be delivered by motors "M" of handle assembly 12 to adapter assembly 14 during operation of motors "M," selection of which motors "M" of handle assembly 12 are to be actuated, functions of end effector 26 of surgical loading unit 15 to be performed by handle assembly 12, or the like). Each set of operating parameters of handle assembly 12 is designed to drive the actuation of a specific set of functions unique to respective types of end effectors when an end effector is coupled to handle assembly 12. For example, handle assembly 12 may vary its power output, deactivate or activate certain buttons thereof, and/or actuate different motors "M" thereof depending on which type of surgical loading unit is coupled to handle assembly 12.

The actuation of motors "M" of handle assembly 12 function to drive shafts and/or gear components (not shown) of adapter assembly 14 in order to drive the various operations of surgical loading unit 15 attached thereto. In particular, when surgical loading unit 15 is coupled to handle assembly 12, motors "M" are configured to drive the shafts and/or gear components of adapter assembly 14 in order to selectively move an anvil assembly 30 of end effector 26 of surgical loading unit 15 relative to a circular cartridge assembly 28 of end effector 26 of surgical loading unit 14, to fire staples from within cartridge assembly 28, and to advance an annular knife blade (not shown) from within circular cartridge assembly 28.

Handle housing 16 further includes a processor "P," for example, a microprocessor. Processor "P" is configured to determine if and when an identification code stored in a memory 50 (FIG. 2) of adapter assembly 14 corresponds to the type of surgical loading unit that is operatively coupled to handle assembly 12. Processor "P" is configured to disable operation of motors "M" of handle assembly 12 when the identification code stored in memory 50 does not correspond to a particular type of surgical loading unit 15 and/or adapter assembly 14 coupled to handle assembly 12. For example, if the identification code stored in memory 50 corresponds to an endo-gastrointestinal anastomosis surgical loading unit (not shown) and, if the illustrated circular end-to-end anastomosis loading unit 15 is coupled to handle assembly 12, a negative identification will be made by processor "P" and handle assembly 12 will be rendered inoperable.

Handle assembly 12 further includes a battery "B" disposed in a base portion thereof. Battery "B" provides power to motors "M" upon actuation of the trigger of handle assembly 12.

With continued reference to FIG. 1, adapter assembly 14 of surgical instrument 10 is configured to couple surgical loading unit 15 to handle assembly 12. Adapter assembly 14 includes a knob housing 20 and an elongate body 22 extending distally from a distal end of knob housing 20. Knob housing 20 and elongate body 22 are configured and dimensioned to house the components of adapter assembly 14. Elongate body 22 is dimensioned for endoscopic insertion. For example, elongate body 22 is passable through a typical trocar port, cannula, or the like. Knob housing 20 is dimensioned to not enter the trocar port, cannula, or the like. Elongate body 22 of adapter assembly 14 has a proximal portion 22a coupled to knob housing 20 and a distal portion 22b configured to be coupled to surgical loading unit 15. Adapter assembly 14 converts a rotation of drive elements (not shown) of handle assembly 12 into axial movement of driven members (not shown) of adapter assembly 14 to actuate functions of loading unit 15.

An exemplary embodiment of an adapter assembly is disclosed in U.S. Patent Application Publication No. 2013/0324978, filed on May 2, 2013, the entire contents of which are incorporated by reference herein.

With continued reference to FIG. 1, surgical loading unit 15 of surgical instrument 10 has a proximal end having an elongate body 24 and a distal end having an end effector 26 supported on elongate body 24. Elongate body 24 is releasably coupled to distal end 22b of elongate body portion 22 of adapter assembly 14. In some embodiments, elongate body 24 of surgical loading unit 15 may be monolithically formed with or integrally connected to distal end 22b of elongate body 22 of adapter assembly 14.

End effector 26 of loading unit 15 includes a cartridge assembly 28 and an anvil assembly 30. Cartridge assembly 28 is releasably mounted to distal end 24b of elongate body 24. Cartridge assembly 28 includes a staple cartridge 32 configured for supporting a plurality of surgical staples (not shown) therein and to discharge the staples into tissue after approximation of cartridge assembly 28 and anvil assembly 30. Staple cartridge 32 has a plurality of staple retaining recesses 33 having the surgical staples disposed therein. Staple retaining recesses 33 are arranged in annular rows. It is envisioned that cartridge assembly 28 may be operably mounted to a distal end of any actuation assembly, powered or manual, of various surgical instruments.

Anvil assembly 30 includes, inter alia, an anvil shaft 36, an anvil head 38, and an anvil center rod 40 extending from anvil head 38. Anvil shaft 36 extends from elongate body 24 of loading unit 15. A proximal end (not shown) of anvil shaft 36 is configured to be removably or non-removably coupled to a central shaft 16 of adapter assembly 14. As known in the art, central shaft 16 of adapter assembly 14 is operable to selectively longitudinally move anvil shaft 36 to move anvil head 38, which is supported on anvil shaft 36, between unapproximated and approximated positions, in relation to cartridge assembly 28, in response to actuation of handle assembly 12.

With reference to FIG. 2, surgical instrument 10 further includes a flex circuit 100, which is disposed or disposable within adapter assembly 14 and configured to electrically connect electrical components (e.g., a memory 50, a linear position sensor assembly 60, and a pressure sensor 70, or the like) of adapter assembly 14 to processor "P" of handle assembly 12. In particular, flex circuit 100 extends longitudinally through adapter assembly 14 and has a proximal end 100a and a distal end 100b. Proximal end 100a of flex circuit 100 is configured to be electrically connected, directly or indirectly, to processor "P" of handle assembly 12. Distal end 100b of flex circuit 100 is configured to be electrically connected, directly or indirectly, to memory 50, linear position sensor assembly 60, and pressure sensor 70, as will be described in greater detail below.

In some embodiments, distal end 100b of flex circuit 100 may be configured to be electrically connected to certain electrical components (e.g., a memory, a linear position sensor assembly, and/or a pressure sensor, or the like) disposed in surgical loading unit 15 rather than in adapter assembly 14 or in addition to those disposed in adapter assembly 14.

With reference to FIGS. 2 and 3A-3C, flex circuit 100 comprises two surface layers 102, 104 stacked upon one another. It is contemplated that flex circuit 100 may include one or more than two surface layers. First and second surface layers 102, 104 bifurcate from one another (see FIG. 2) at distal end 100b of flex circuit 100 to form a first distal end 102b of flex circuit 100 and a second distal end 104b of flex circuit 100. First distal end 102b of flex circuit 100 electrically connects to both memory 50 and linear position sensor assembly 60. Second distal end 104b of flex circuit 100 electrically connects to pressure sensor 70. Proximal ends 102a, 104a of each of surface layers 102, 104 electrically connect, directly or indirectly, to processor "P" to electrically couple processor "P" to memory 50, linear position sensor assembly 60, and pressure sensor 70.

Proximal and distal ends 102a, 102b of first surface layer 102 of flex circuit 100 each have seven (7) contacts "C1-C7," "C8-C14." Two contacts "C13," "C14" of the seven (7) contacts "C8-C14" of distal end 102b of first surface layer 102 are associated with memory 50, and two contacts "C1," "C2" of the seven (7) contacts "C" of proximal end 102a of first surface layer 102 are associated with processor "P" for transmitting information between processor "P" of handle assembly 12 and memory 50 of adapter assembly 14. The other five (5) contacts "C8-C12" of the seven (7) contacts "C8-C14" of distal end 102b of first surface layer 102 are associated with linear position sensor assembly 60, and the other five (5) contacts "C3-C7" of the seven (7) contacts "C1-C7" of proximal end 102a of first surface layer 102 are associated with processor "P" for transmitting information between processor "P" of handle assembly 12 and linear position sensor assembly 60 of adapter assembly 14.

Proximal and distal ends 104a, 104b of second surface layer 104 of flex circuit 100 each have five (5) contacts "C15-C19," "C20-C24." The five (5) contacts "C20-C24" of distal end 104b of second surface layer 104 are associated with pressure sensor 70, and the five (5) contacts "C15-C19" of proximal end 104a of second surface layer 104 are associated with processor "P" for transmitting information between processor "P" of handle assembly 12 and pressure sensor 70 of adapter assembly 14. In some embodiments, first and second surface layers 102, 104 may have fewer or more than 7 or 5 contacts, respectively.

With continued reference to FIG. 2, as mentioned above, adapter assembly 14 includes a plurality of electrical components, e.g., a memory 50, a linear position sensor assembly 60, and a pressure sensor 70. Memory 50 of adapter assembly 14 is disposed within distal end 22b (FIG. 1) of elongate body 22 and is electrically coupled to first distal end 102b of flex circuit 100. It is contemplated that memory 50 may be a non-volatile memory, such as, for example, a 1-wire electrically erasable programmable read-only memory. Memory 50 has stored therein discrete operating parameters of handle assembly 12 that correspond to the operation of one type of surgical loading unit, for example, surgical loading unit 15, and/or one type of adapter assembly, for example, adapter assembly 14. The operating parameter(s) stored in memory 50 can be at least one of: a speed of operation of motors "M" of handle assembly 12; an amount of power to be delivered by "M" of handle assembly 12 during operation thereof; which motors "M" of handle assembly 12 are to be actuated upon operating handle assembly 12; types of functions of surgical loading unit 15 to be performed by handle assembly 12; or the like.

Memory 50 may also have a discrete identification code or serial number stored therein that corresponds to one type of surgical loading unit and/or one type of adapter assembly. The identification code stored in memory 50 indicates the type of surgical loading unit and/or adapter assembly to which handle assembly 12 is intended to be used.

Figure 4:
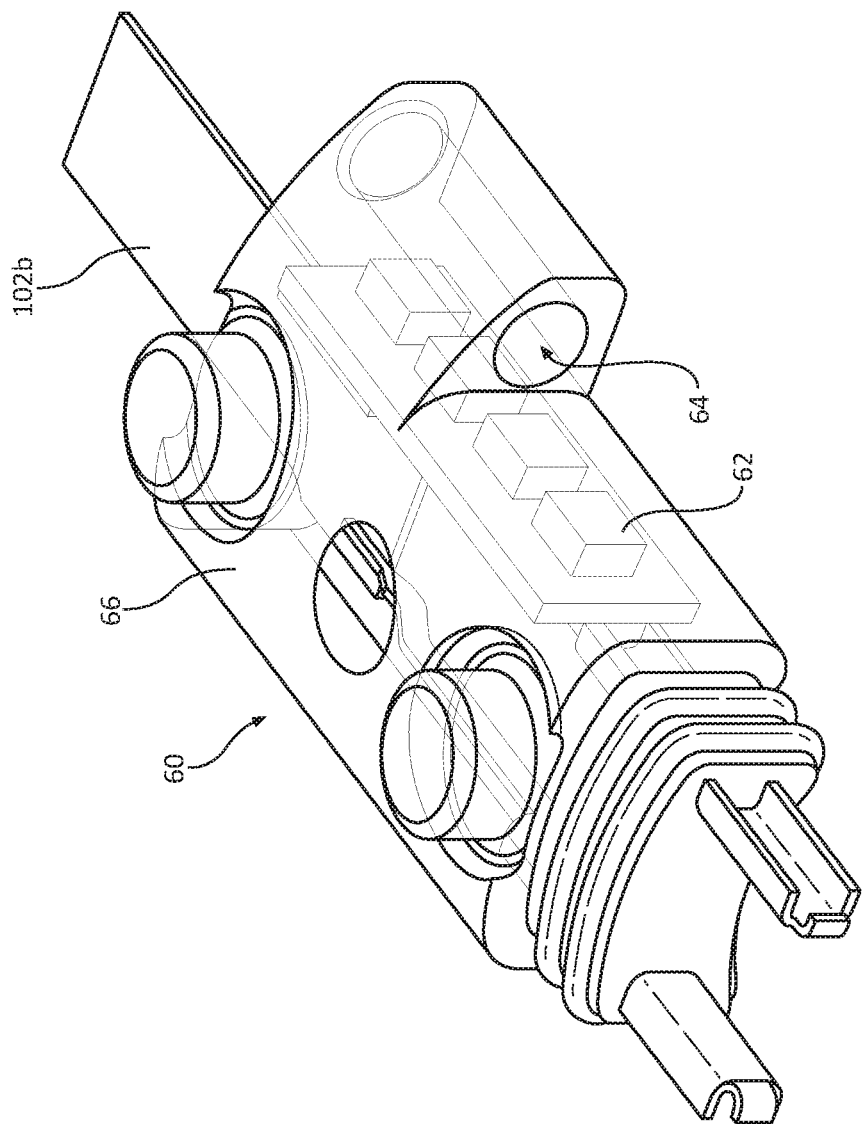
FIG. 4 is a perspective view of a linear position sensor assembly connected to the flex circuit of FIG. 2.

With reference to FIGS. 1, 2 and 4, linear position assembly 60 of adapter assembly 14 is partially disposed within distal end 22b of elongate body 22 and is electrically coupled to first distal end 102b of flex circuit 100. Linear position assembly 60 includes a plurality of sensors 62 axially aligned with one another. Linear position sensor assembly 60 further includes magnets (not shown) mounted on central shaft 16 of adapter assembly 14. As such, the magnets move with central shaft 16 as central shaft 16 moves relative to cartridge assembly 28 between the unapproximated and approximated positions. Central shaft 16 is configured for slidable receipt in a channel 64 defined in a housing 66 of linear position sensor assembly 60. In some embodiments, the magnets may be supported on or disposed in various components of anvil assembly 30. The magnets generate a magnetic field that is detected by sensors 62 and used to ultimately determine a linear position of anvil assembly 30 relative to cartridge assembly 28.

Sensors 62 are configured to sense a change in the magnetic field emitted by the magnets upon longitudinal movement of the magnets relative to sensors 62 as central shaft 16 is displaced or moved axially through channel 64 of linear position sensor assembly 60. Sensors 62 may be in the form of magnetoresistance sensors. As such, magnetoresistance sensors 62 are configured to sense or determine an angle of direction of the magnetic field emitted by the magnets throughout relative longitudinal movement of the magnets. In some embodiments, sensors 62 may be in the form of hall-effect sensors. Hall-effect sensors are configured to sense or determine a magnetic flux density of the magnetic field emitted by the magnets throughout relative longitudinal movement of the magnets.

Figure 5:
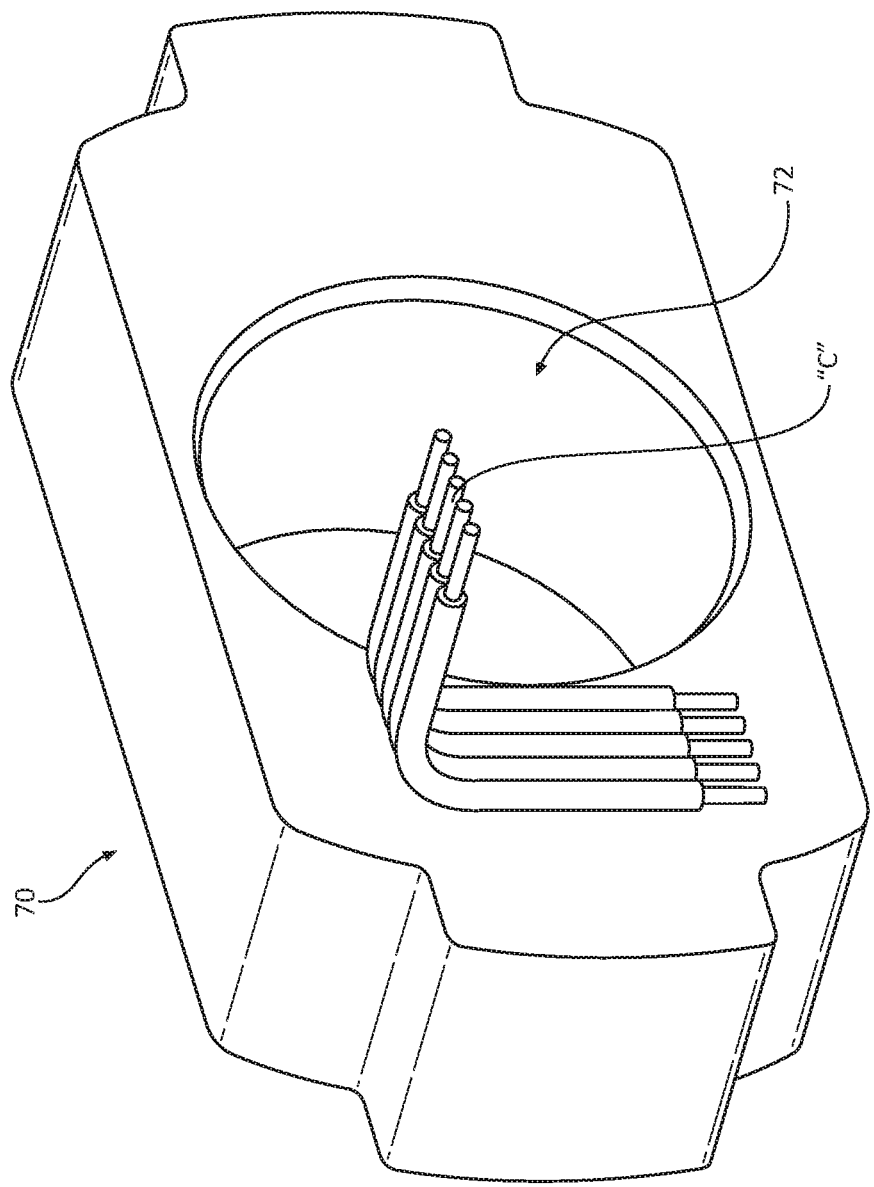
FIG. 5 is a perspective view of a pressure sensor.

With reference to FIGS. 2 and 5, pressure sensor or strain gauge 70 of adapter assembly 14 is disposed within distal end 22b of elongate body 22 and is electrically coupled to second distal end 104b of flex circuit 100. Pressure sensor 70 is designed and adapted to detect, measure, and relay to handle assembly 12 an axial force output and/or input of adapter assembly 14. In particular, drive shafts (not shown) of adapter assembly 14 are operably coupled to strain gauge 70 and extend through a channel 72 defined through strain gauge 70. As strain gauge 60 enters a compressed and/or tensioned condition by a force imparted thereon by movement of the drive shafts of adapter assembly 14, an electrical resistance of strain gauge 60 is changed, which is measured by a circuit board, such as, for example, a wheatstone bridge (not shown). The measured change in electrical resistance of strain gauge 60 is then related to the amount strain gauge 60 has been strained (e.g., bent). The calculated strain is then correlated to an amount of axial force output of adapter assembly 14.

For a detailed discussion of an exemplary pressure sensor, reference may be made to U.S. patent application Ser. No. 14/662,731, filed on Mar. 30, 2015, entitled "Adapter Assemblies For Interconnecting Electromechanical Handle Assemblies and Surgical Loading Units," the entire contents of which are incorporated by reference herein.

In use, a particular surgical procedure is selected, such as, for example, a thoracic surgery having a unique and/or specific set of surgical operating parameters/requirements/tasks. Accordingly, a desired/necessary adapter assembly, e.g., adapter assembly 14, is selected from a plurality of adapter assemblies available for use in order to achieve the surgical operating parameter/requirement/task. Proximal end 100a of flex circuit 100 of adapter assembly 14 is connected to processor "P" of handle assembly 12 and distal end 100b of flex circuit 100 is connected to each of the electrical components of adapter assembly 14 (e.g., memory 50, linear position sensor assembly 60, and pressure sensor 70).

Upon directly or indirectly electrically connecting processor "P" of handle assembly 12 to memory 50 of adapter assembly 14 via flex circuit 100, processor "P" receives, from memory 50, the parameter(s) by which handle assembly 12 will operate during use, including, for example, a set of parameters tailored for the operation of adapter assembly 14. Upon directly or indirectly electrically connecting processor "P" to linear position sensor assembly 60 of adapter assembly 14 via flex circuit 100, processor "P" is able to receive information from linear position sensor assembly 60 involving the linear position of anvil assembly 30 of surgical loading unit 15 relative to cartridge assembly 28 of surgical loading unit 15. Upon directly or indirectly electrically connecting processor "P" of handle assembly 12 to pressure sensor 70 of adapter assembly 14 via flex circuit 100, processor "P" is able to receive information from pressure sensor 70 involving an amount of axial force output or input of adapter assembly 14.

Figure 6:
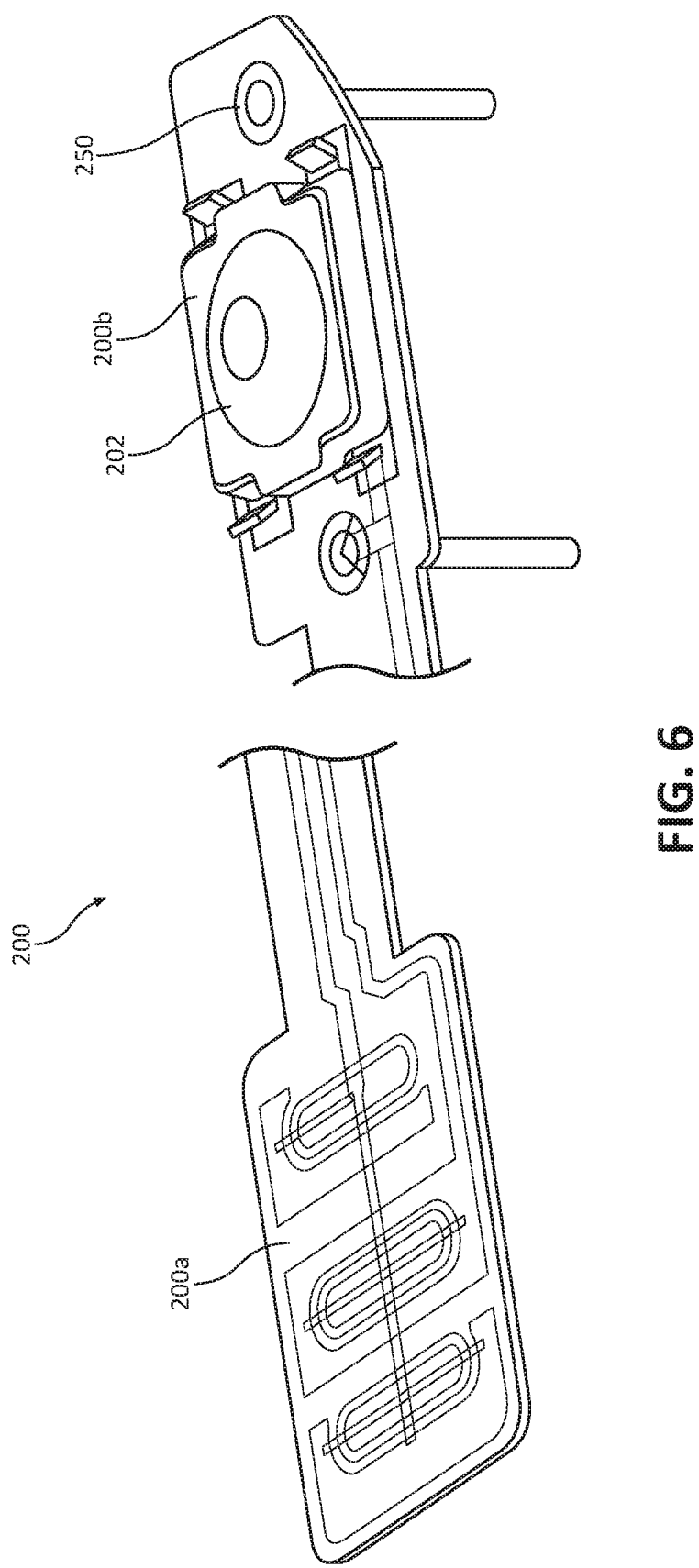
FIG. 6 is an embodiment of a flex circuit having a switch disposed at a distal end thereof.

With reference to FIG. 6, provided is an embodiment of a flex circuit 200, similar to flex circuit 100 described above with reference to FIGS. 1-5. Flex circuit 200 is configured to be assembled within an adapter assembly, for example, adapter assembly 14 of FIG. 1. Flex circuit 200 has a proximal end 200a and a distal end 200b. Proximal end 200a of flex circuit 200 is configured to be electrically connected, directly or indirectly, to processor "P" (FIG. 1) of handle assembly 12. Distal end 200b of flex circuit 200 has a switch 202 configured to be activated by a surgical loading unit, e.g., an endo-gastrointestinal anastomosis surgical loading unit (not shown) upon proper connection of the surgical loading unit to adapter assembly 14. Flex circuit 200 also has a memory 250, similar to memory 50 described above, that has stored therein operating parameters of handle assembly 12 (FIG. 1).

In use, upon properly connecting the surgical loading unit with adapter assembly 14, memory 250 of flex circuit 200 automatically transmits the operating parameters stored therein to processor "P" via flex cable 200. If the surgical loading unit is not properly connected to adapter assembly 14, or the wrong surgical loading unit is connected to adapter assembly 14, switch 202 of flex circuit 200 will not be activated such that handle assembly 12 will not be operable to actuate functions of the surgical loading unit.

In some embodiments, flex circuit 200 may also be configured to electrically connect, in addition to switch 202, other electrical components (e.g. a linear position sensor assembly and/or a pressure sensor) of adapter assembly 14 to processor "P" of a handle assembly, e.g., handle assembly 12 of FIG. 1.

It will be understood that various modifications may be made to the embodiments of the presently disclosed surgical instrument 10 and components thereof. Therefore, the above description should not be construed as limiting, but merely as exemplifications of embodiments. Those skilled in the art will envision other modifications within the scope and spirit of the present disclosure.

The invention claimed is:

1. A surgical instrument, comprising:
a handle assembly including:
a handle housing; and
a processor disposed within the handle housing; and
an adapter assembly configured to convert a rotation of drive elements of the handle assembly into axial movement of driven members of the adapter assembly to actuate functions of an end effector of a surgical loading unit, the adapter assembly including:
a knob housing configured to be connected to the handle housing;
an elongate body extending distally from the knob housing and having a distal end configured to be coupled to the end effector;
a plurality of electrical components disposed within the elongate body; and
a flex circuit extending longitudinally through the knob housing and the elongate body and having a proximal end configured to be electrically connected to the processor, and a distal end configured to be electrically connected to the plurality of electrical components.

2. The surgical instrument according to claim 1, wherein the flex circuit includes at least two surface layers stacked upon one another, a first surface layer of the at least two surface layers being configured to electrically couple the processor to two of the plurality of electrical components, and a second surface layer of the at least two surface layers being configured to electrically couple the processor to another of the plurality of electrical components.

3. The surgical instrument according to claim 1, wherein the distal end of the flex circuit includes a switch configured to be activated by one type of end effector upon connection of the one type of end effector to the distal end of the elongate body, whereby a memory of the flex circuit transmits operating parameters of the adapter assembly to the processor.

4. The surgical instrument according to claim 1, wherein one of the plurality of electrical components is a linear position sensor assembly that is disposed in the distal end of the elongate body, and wherein the distal end of the flex circuit is electrically and mechanically connected to the linear position sensor assembly.

5. The surgical instrument according to claim 4, wherein the linear position sensor assembly includes plurality of sensors axially aligned with one another along a longitudinal axis of the linear position sensor assembly.

6. The surgical instrument according to claim 4, wherein the linear position sensor assembly has five contacts electrically connected to the distal end of the flex circuit.

7. The surgical instrument according to claim 4, wherein another of the plurality of electrical components is a pressure sensor, the distal end of the flex circuit being bifurcated forming a first distal end electrically and mechanically connected to the linear position sensor assembly and a memory, and a second distal end electrically and mechanically connected to the pressure sensor, the second distal end extending in a generally proximal direction and disposed proximally of the first distal end.

8. The surgical instrument according to claim 7, wherein the pressure sensor is a strain gauge.

9. The surgical instrument according to claim 7, wherein the pressure sensor has five contacts electrically connected to the second distal end of the flex circuit.

10. The surgical instrument according to claim 1, wherein one of the plurality of electrical components is a memory having stored therein at least one operating parameter of the surgical instrument, the distal end of the flex circuit being electrically connected to the memory.

11. The surgical instrument according to claim 10, wherein the at least one operating parameter is selected from the group consisting of a speed of operation of a motor of the handle assembly, an amount of power to be delivered by the motor of the handle assembly during operation thereof, a selection of which motors of the handle assembly are to be actuated, and a type of function of an end effector to be performed by the handle assembly.

12. The surgical instrument according to claim 10, wherein the memory has an identification code stored therein corresponding to one type of end effector.

13. The surgical instrument according to claim 1, wherein the memory is a 1-wire eeprom having two contacts electrically and mechanically connected to the distal end of the flex circuit.

14. A surgical instrument, comprising:
a handle assembly including:
a handle housing;
a motor disposed within the handle housing; and
a processor disposed within the handle housing;
an adapter assembly configured to convert a rotation of drive elements of the handle assembly into axial movement of driven members of the adapter assembly to actuate functions of an end effector of a surgical loading unit, the adapter assembly including:
a knob housing configured to be connected to the handle housing;
an elongate body extending distally from the knob housing and having a distal end;
a plurality of electrical components disposed within the elongate body; and
a flex circuit extending longitudinally through the knob housing and the elongate body and having a proximal end configured to be electrically connected to the processor, and a distal end configured to be electrically connected to the plurality of electrical components; and
the surgical loading unit having a proximal end configured to be operably coupled to the distal end of the elongate body of the adapter assembly and a distal end having the end effector.

15. The surgical instrument according to claim 14, wherein the flex circuit includes at least two surface layers stacked upon one another, a first surface layer of the at least two surface layers being configured to electrically couple the processor to two of the plurality of electrical components, and a second surface layer of the at least two surface layers being configured to electrically couple the processor to another of the plurality of electrical components.

16. The surgical instrument according to claim 15, wherein a first electrical component of the plurality of electrical components is a linear position sensor assembly that is disposed in the distal end of the elongate body, a distal end of the first surface layer of the at least two surface layers of the flex circuit being electrically and mechanically connected to the linear position sensor assembly.

17. The surgical instrument according to claim 16, wherein a second electrical component of the plurality of electrical components is a pressure sensor, a distal end of the second surface layer of the at least two surface layers of the flex circuit being bifurcated from the first surface layer and having a distal end electrically and mechanically connected to the pressure sensor.

18. The surgical instrument according to claim 17, wherein a third electrical component of the plurality of electrical components is a memory having stored therein at least one operating parameter of the surgical instrument, the distal end of the first surface layer of the at least two surface layers of the flex circuit being electrically connected to the memory.

19. The surgical instrument according to claim 18, wherein the distal end of the flex circuit includes a switch configured to be activated by the surgical loading unit upon connection of the surgical loading unit to the adapter assembly such that upon connecting the surgical loading unit with the adapter assembly, the memory automatically transmits the at least one operating parameter to the processor via the flex circuit.

20. The surgical instrument according to claim 14, wherein the proximal end of the flex circuit is received in the handle housing when the handle assembly is coupled to the adapter assembly, and wherein a majority of a length of the flex circuit remains disposed within the adapter assembly when the proximal end of the surgical loading unit is separated from the distal end of the elongate body.

\* \* \* \* \*